(12) United States Patent
Tiao et al.

(10) Patent No.: US 10,520,436 B2
(45) Date of Patent: Dec. 31, 2019

(54) DYNAMIC FOCUSING CONFOCAL OPTICAL SCANNING SYSTEM

(71) Applicant: Caduceus Biotechnology Inc., Hsinchu (TW)

(72) Inventors: Golden Tiao, Hsinchu (TW); Jung-Po Chen, Hsinchu (TW); Chien-Chung Pien, Hsinchu (TW); Tsung-Kai Chang, Hsinchu (TW); Feng-Hsiang Lo, Hsinchu (TW); Jean-Dow Lee, Hsinchu (TW); Jinn-Cherng Yang, Hsinchu (TW); Rung-Ywan Tsai, Hsinchu (TW)

(73) Assignee: Caduceus Biotechnology Inc., Hsinchu (TW)

( * ) Notice: Subject to any disclaimer, the term of this patent is extended or adjusted under 35 U.S.C. 154(b) by 368 days.

(21) Appl. No.: 15/441,251

(22) Filed: Feb. 24, 2017

(65) Prior Publication Data
US 2018/0149594 A1    May 31, 2018

Related U.S. Application Data

(60) Provisional application No. 62/427,760, filed on Nov. 29, 2016.

(51) Int. Cl.
| | |
|---|---|
| *G01N 21/64* | (2006.01) |
| *G02B 21/00* | (2006.01) |
| *G02B 21/16* | (2006.01) |
| *G02B 21/26* | (2006.01) |
| *F21V 8/00* | (2006.01) |

(52) U.S. Cl.
CPC ....... *G01N 21/6458* (2013.01); *G01N 21/645* (2013.01); *G01N 21/6428* (2013.01);
(Continued)

(58) Field of Classification Search
None
See application file for complete search history.

(56) References Cited

U.S. PATENT DOCUMENTS

| | | | |
|---|---|---|---|
| 5,760,901 A * | 6/1998 | Hill ..................... | G02B 21/004 356/450 |
| 6,185,030 B1 * | 2/2001 | Overbeck ............. | B01L 3/0241 250/586 |

(Continued)

*Primary Examiner* — Neil N Turk
(74) *Attorney, Agent, or Firm* — JCIPRNET (57) ABSTRACT

An optical scanning system adapted to scan a sample on a chip is provided. The optical scanning system includes at least one optical scanning head, at least one scanning light source, a light receiving device and a processor. Each of at least one optical scanning head includes a focusing light source, a first optical guiding structure, and a control unit. The first optical guiding structure is configured to guide the focusing light emitted from the focusing light source to travel to the sample, and the first optical guiding structure is configured to guide the at least one scanning light emitted from the at least one scanning light source to the sample to generate a secondary light. The control unit is configured to control the first optical guiding structure to keep the focusing light and at least one scanning light focusing on a surface of the chip. The light receiving device receives the secondary light and generates a scanning electronic signal. The processor is electrically coupled to the light receiving device to dispose the scanning electronic signal.

15 Claims, 9 Drawing Sheets

(52) U.S. Cl.
CPC ....... *G01N 21/6452* (2013.01); *G02B 6/0005* (2013.01); *G02B 21/006* (2013.01); *G02B 21/0032* (2013.01); *G02B 21/0036* (2013.01); *G02B 21/16* (2013.01); *G02B 21/26* (2013.01); *G01N 2021/6463* (2013.01); *G01N 2021/6484* (2013.01); *G01N 2201/0407* (2013.01); *G01N 2201/0484* (2013.01); *G01N 2201/101* (2013.01); *G01N 2201/11* (2013.01); *G02B 21/004* (2013.01); *G02B 21/0048* (2013.01)

(56) References Cited

U.S. PATENT DOCUMENTS

| | | | |
|---|---|---|---|
| 6,251,601 B1 * | 6/2001 | Bao | C12Q 1/6837 422/400 |
| 6,320,196 B1 * | 11/2001 | Dorsel | G01N 21/6402 250/458.1 |
| 6,399,952 B1 * | 6/2002 | Maher | G01N 21/6428 250/458.1 |
| 6,486,457 B1 | 11/2002 | Dorsel et al. | |
| 6,545,758 B1 * | 4/2003 | Sandstrom | B82Y 30/00 250/458.1 |
| 6,833,916 B2 | 12/2004 | Osipchuk et al. | |
| 6,927,389 B2 | 8/2005 | Curry et al. | |
| 7,706,419 B2 | 4/2010 | Wang et al. | |
| 8,119,391 B2 * | 2/2012 | Kim | B01L 3/0244 435/283.1 |
| 2001/0046712 A1 * | 11/2001 | Hang | G01N 21/6452 436/172 |
| 2002/0074512 A1 | 6/2002 | Montagu et al. | |
| 2006/0033988 A1 * | 2/2006 | Mikuriya | G02B 21/0024 359/385 |
| 2012/0235016 A1 | 9/2012 | Weiner et al. | |
| 2016/0356717 A1 * | 12/2016 | Fujii | G01N 21/648 |
| 2017/0010453 A1 * | 1/2017 | Imoto | G01N 21/6458 |

* cited by examiner

DYNAMIC FOCUSING CONFOCAL OPTICAL SCANNING SYSTEM

CROSS-REFERENCE TO RELATED APPLICATION

This application claims the priority benefit of U.S. provisional application Ser. No. 62/427,760, filed on Nov. 29, 2016. The entirety of the above-mentioned patent application is hereby incorporated by reference herein and made a part of this specification.

BACKGROUND OF THE INVENTION

1. Field of the Invention

The present invention generally relates to a scanning system, in particular, to an optical scanning system.

2. Description of Related Art

In recent years, with the increase of the demand of personalized gene sequencing, the market of reagent detection of gene chips is also grown year by year. Except gene chips, the market of microarray biochips of mRNA, peptide, protein and antibody are also grown with time. Gene microarray chip is mainly formed by disposing deoxyribonucleic acid (DNA) microarray on glass or silicon wafer. Different complementary DNA (cDNA) or oligo-DNA are disposed on the positions of the gene bio-microarray chip, so as to mix with biological samples and standard control samples. In general, fluorescent dyes in different colors like Cy3 (green) and Cy5 (red) will be used to mark the biological samples and the standard control samples. When using excitation light sources in different wavelengths to excite fluorescent dyes, the corresponding fluorescences will be produced. By detecting the positions of the fluorescences, the sequences and the structures of DNA can be learned. Besides, by detecting the luminous intensity of the fluorescence, the concentration of DNA having specific structure can be learned.

In general, lots of test points are disposed on the gene microarray chip. For example, tens of thousands of test points are disposed on 1-inch×3-inches gene microarray chip, and the size of each test point is about 80 to 100 micrometers. For precisely interpretation and analysis of the gene microarray chip, the biochip scanner with high resolution is needed to use to interpret the image and signal strength of the biochip, so as to determine gene type or gene structure and its corresponding concentration. In addition, the biochip scanner has to include two or more excitation light sources for exciting different fluorescent dyes. Therefore, how to fast and precisely excite fluorescent dyes to detect the biochip in one test process and to obtain a large number of gene sequences related information, is the research focus of the field.

SUMMARY OF THE INVENTION

The present disclosure is directed to an optical scanning system capable of keeping the scanning light focusing on the sample, so as to achieve fast and precise optical detection of the sample structure and concentration.

An optical scanning system is adapted to scan a sample on a chip. The optical scanning system includes at least one optical scanning head, at least one scanning light source, a light receiving device and a processor. Each of the at least one optical scanning head includes a focusing light source, a first optical guiding structure and a control unit coupled to the first optical guiding structure. The focusing light source is adapted to emit a focusing light. The first optical guiding structure is disposed on a transmission path of the focusing light, and configured to guide the focusing light to travel to the sample. The at least one scanning light source is adapted to emit at least one scanning light. The first optical guiding structure is configured to guide the at least one scanning light to the sample to generate a secondary light. The control unit is configured to control the first optical guiding structure to keep the focusing light and the at least one scanning light focusing on a surface of the chip. The light receiving device is disposed on a transmission path of the secondary light to receive the secondary light and generate a scanning electronic signal. The processor is electrically coupled to the light receiving device to dispose the scanning electronic signal.

Based on the above, in the optical scanning system provided by embodiments of the present disclosure, because the control unit is configured to control the first optical guiding structure to keep the focusing light and the at least one scanning light focusing on the surface of the chip, the optical scanning system is capable of keeping the at least one scanning light focusing on the sample surface, so as to achieve fast and precise optical detection.

To make the above features and advantages of the present disclosure more comprehensible, several embodiments accompanied with drawings are described in detail as follows.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Reference will now be made in detail to the present preferred embodiments of the invention, examples of which are illustrated in the accompanying drawings. Wherever possible, the same reference numbers are used in the drawings and the description to refer to the same or like parts.

Figure 1:
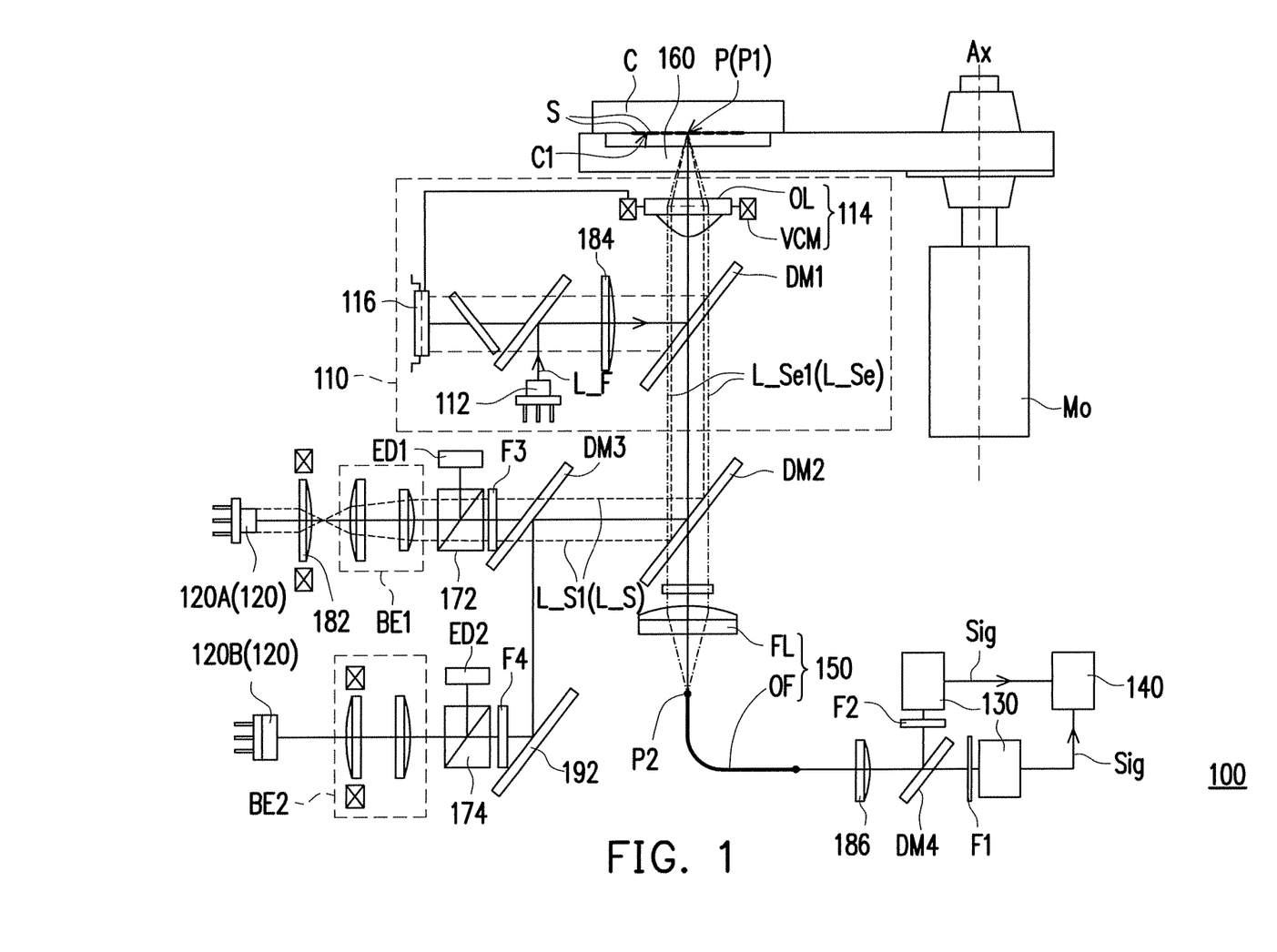
FIG. 1 is a schematic diagram of an optical scanning system in an embodiment of the present disclosure.

FIG. 1 is a schematic diagram of an optical scanning system in an embodiment of the present disclosure. Referring to FIG. 1, in the embodiment, an optical scanning system 100 is adapted to scan a sample S on a chip C. The optical scanning system 100 includes at least one optical scanning head 110, at least one scanning light source 120, a light receiving device 130 and a processor 140. In particular, the optical scanning system 100 has an optical scanning head 110, and the optical scanning head 110 includes a focusing light source 112, a first optical guiding structure 114 and a control unit 116 coupled to the first optical guiding structure 114. The focusing light source 112 is adapted to emit a focusing light L_F. The first optical guiding structure 114 is disposed on a transmission path of the focusing light L_F, and configured to guide the focusing light L_F to travel to the surface C1 of the chip C so that the focusing light L_F is guided to the sample S. To be specific, the chip C is made of glass, but the invention is not limited thereto.

In the embodiment, the at least one scanning light source 120 is adapted to emit at least one scanning light L_S, and the first optical guiding structure 114 is configured to guide the at least one scanning light L_S to the surface C1 of the chip C so that the at least one scanning light L_S is guided to the sample S to generate a secondary light L_Se. The control unit 116 is, for example, includes a photodetector. The photodetector of the control unit 116 is configured to receive the focusing light L_F returned from the surface C1 of the chip C, and the control unit 116 is, for example, configured to send a servo signal to a voice coil motor VCM of the first optical guiding structure 114 to keep the focusing light L_F and the at least one scanning light L_S focusing on the same surface C1 of the chip C. Since the sample S has a relatively thin thickness and the thickness may be within the focus depth of the focusing light, the focusing light L_F and the at least one scanning light L_S may be kept focusing on the same surface of the sample S. In particular, the chip C is a biochip, for example, a bio-microarray chip, and the sample is a biological sample. The optical scanning system 100 is, for example, an optical system of the bio-microarray chip scanner. Besides, for example, the sample S includes a fluorescent dye, and the at least one scanning light L_S is configured to stimulate the fluorescent dye to generate the secondary light L_Se. To be specific, the secondary light L_Se is, for example, a fluorescence.

In the embodiment, the at least one scanning light source 120 includes a first scanning light source 120A and a second scanning light source 120B. The first scanning light source 120A is adapted to emit a first scanning light L_S1, and the second scanning light source 120B is adapted to emit a second scanning light (not shown). The first optical guiding structure 114 is configured to guide the first scanning light L_S1 and the second scanning light L_S2 to the sample S to generate a first secondary light L_Se1 and a second secondary light (not shown), respectively. Besides, a wavelength of the first scanning light L_S1 is different from a wavelength of the second scanning light (not shown). To be specific, for example, the sample S includes a green fluorescent dye Cy3 and a red fluorescent dye Cy5, and the first scanning light L_S1 emitted from the first scanning light source 120A is a laser light having a 635 nanometers wavelength and configured to stimulate the red fluorescent dye Cy5. Besides, the second scanning light (not shown) emitted from the second scanning light source 120B is a laser light having a 520 nanometers wavelength and configured to stimulate the green fluorescent dye Cy3. However, in some embodiments, the sample S may further include the fluorescent dye of other color, and the optical scanning system 100 may include the scanning light source corresponding to the excitation wavelength of the fluorescent dye, which is not limited by the invention.

In the embodiment, the focusing light L_F emitted from the focusing light source 112 is, for example, a laser light having 780 nanometers wavelength, and the focusing light L_F is configured to dynamically focus and servo control. To be specific, the first optical guiding structure 114 includes an objective lens OL and the voice coil motor VCM. The focusing light L_F and the at least one scanning light L_S pass through the objective lens OL, and the focusing light L_F and the at least one scanning light L_S focus on an identical focal point P. For example, the control unit 116 can send a servo signal to the voice coil motor VCM of the first optical guiding structure 114, and the voice coil motor VCM may adjust a distance between the objective lens OL and the surface C1 of the chip C so as to keep the focal point P located on the surface C1 of the chip C by means of moving upward or moving downward of the objective lens OL. When the control unit 116 controls the first optical guiding structure 114 so that the focusing light L_F focuses on the surface C1 of the chip C, the first scanning light L_S1 and the second scanning light (not shown) will naturally focus on the surface C1 of the chip C, so that the first scanning light L_S1 and the second scanning light (not shown) will naturally focus on the surface of the sample S. For example, in an embodiment, the first optical guiding structure 114 is capable of controlling the focusing light L_F with 780 nanometers wavelength, the first scanning light L_S1 with 635 nanometers wavelength and the second scanning light with 520 nanometers wavelength to focus on the surface C1 of the chip C. At this time, the size of the spot of the focusing light L_F on the surface C1 of the chip C is about 0.944 micrometers, the size of the spot of the first scanning light L_S1 on the surface C1 of the chip C is about 1.041 micrometers, and the size of the spot of the second scanning light on the surface C1 of the chip C is about 1.216 micrometers. In other words, the size of the spots of the lights on the surface C1 of the chip C are about 1 micrometer, namely, the lights have good confocal characteristics and the optical scanning system 100 has an excellent optical resolution.

In the embodiment, the optical scanning system 100 further includes a second optical guiding structure 150, disposed on a transmission path of the secondary light L_Se. For example, the second optical guiding structure 150 includes a focusing lens FL and an optical fiber OF. In particular, the focal point P of the focusing light L_F and the at least one scanning light L_S focus on is a first focal point P1, and the focusing lens FL of the second optical guiding structure 150 focuses the secondary light L_Se on a second focal point P2. Besides, the light receiving device 130 is disposed on the transmission path of the secondary light L_Se to receive the secondary light L_Se. To be specific, an end of the optical fiber OF is located on the second focal point P2 to receive the secondary light L_Se. The optical fiber OF may receive the secondary light L_Se and guide the secondary light L_Se to the light receiving device 130. The light receiving device 130 may receive the secondary light L_Se and generate a scanning electronic signal Sig. Besides, the processor 140 is electrically coupled to the light receiving device 130 to dispose the scanning electronic signal Sig. By disposing the scanning electronic signal Sig corresponding to the sample S, the image detection of the sample S can be achieved. The optical scanning system 100 may be, for example, configured to detect a Deoxyribonucleic acid (DNA) located on the sample S, to present an intensity of the measured DNA, which is not limited by the invention. The other materials, such as mRNA, peptide, protein, antibody, and tissue etc., can be measured by using the mechanism abovementioned to scan the corresponsive bio-microarrays. In the embodiment, a diameter of the optical fiber OF is in a range of 10 micrometers to 200 micrometers, which is not limited by the invention.

In the embodiment, the first focal point P1 and the second focal point P2 form conjugate focal points. That is, the optical scanning system 100 is a dynamic focusing confocal optical scanning system. When the secondary light L_Se focuses on the second focal point P2 and enters the optical fiber OF, by proper selection of the diameter of the optical fiber OF, the stray light not located on the focal point of the secondary light L_Se will not enter the optical fiber OF and be received by the light receiving device 130. Therefore, the signal obtained by detecting the sample S by using the optical scanning system 100 can has good signal to noise ratio (SNR) quality. Besides, in some embodiments, the second optical guiding structure 150 may also include a focusing lens FL and a pinhole device. The focusing lens FL is configured to focus the secondary light L_Se on the second focal point P2, the pinhole device has a pinhole, and the second focal point P2 is located at the pinhole. The pinhole device allows the secondary light L_Se passed through the second focal point P2 passing through the pinhole. To be specific, in these embodiments, by proper selection of the diameter of the pinhole, the stray light not located on the focal plane of the secondary light L_Se will not pass through the pinhole and not be received by the light receiving device 130.

In the embodiment, for example, the light receiving device 130 includes a photon multiplex tube (PMT) or an avalanche photo diode (APD), and can receive the secondary light L_Se and generate the scanning electronic signal Sig. To be specific, the optical scanning system 100 further includes a dichroic device DM4, located between the optical fiber OF and the light receiving device 130. For example, the dichroic device DM4 has a wavelength selectivity. The dichroic device DM4 may reflect a portion of a light with stop band wavelengths and be transparent to the other portion of the light with pass band wavelengths, wherein the portion of the light has a specific wavelength. In some embodiments, the dichroic device DM4 may be transparent to a portion of a light and reflect the other portion of the light, wherein the portion of the light has a specific wavelength. In the embodiment, the secondary light L_Se includes the first secondary light L_Se1 and the second secondary light (not shown), and the dichroic device DM4 is configured to separate the first secondary light L_Se1 from the second secondary light, so that the first secondary light L_Se1 and the second secondary light can be received by the light receiving device respectively. In addition, the processor 140 is, for example, a central processing unit (CPU) or other programmable microprocessor, digital signal processor (DSP), programmable controller, application specific integrated circuits (ASIC), programmable logic device (PLD) or other similar device, which is not limited by the invention.

In the embodiment, the optical scanning system 100 further includes a plurality of optical devices, the optical devices include beam splitters 172, 174, light collimators 182, 184, 186, a reflector 192, optical beam expanders BE1, BE2, dichroic devices DM1, DM2, DM3, DM4 and filters F1, F2, F3, F4 disposed on the transmission path of the focusing light L_F, the scanning light L_S or the secondary light L_Se abovementioned. To be specific, the optical devices abovementioned are configured to at least properly adjust the optical properties of the focusing light L_F, the scanning light L_S or the secondary light L_Se abovementioned. The type and the quantity of the optical devices abovementioned are not limited thereto. Besides, in the embodiment, the optical scanning system 100 further includes power detecting elements ED1 and ED2, configured to detect the power of the first scanning light L_S1 and the power of the second scanning light respectively, for example. As a result, the first scanning light L_S1 and the second scanning light having proper power strength can be provided to the sample, so as to generate the secondary light L_Se.

In the embodiment, because the control unit 116 of the optical scanning system 100 is configured to control the first optical guiding structure 114 to keep the focusing light L_F and the at least one scanning light L_S focusing on the surface C1 of the chip C, the optical scanning system 100 is capable of keeping the at least one scanning light L_S focusing on the surface C1 of chip C, so as to make the at least one scanning light L_S focus on the sample S and achieve fast and precise optical detection.

Figure 2A:
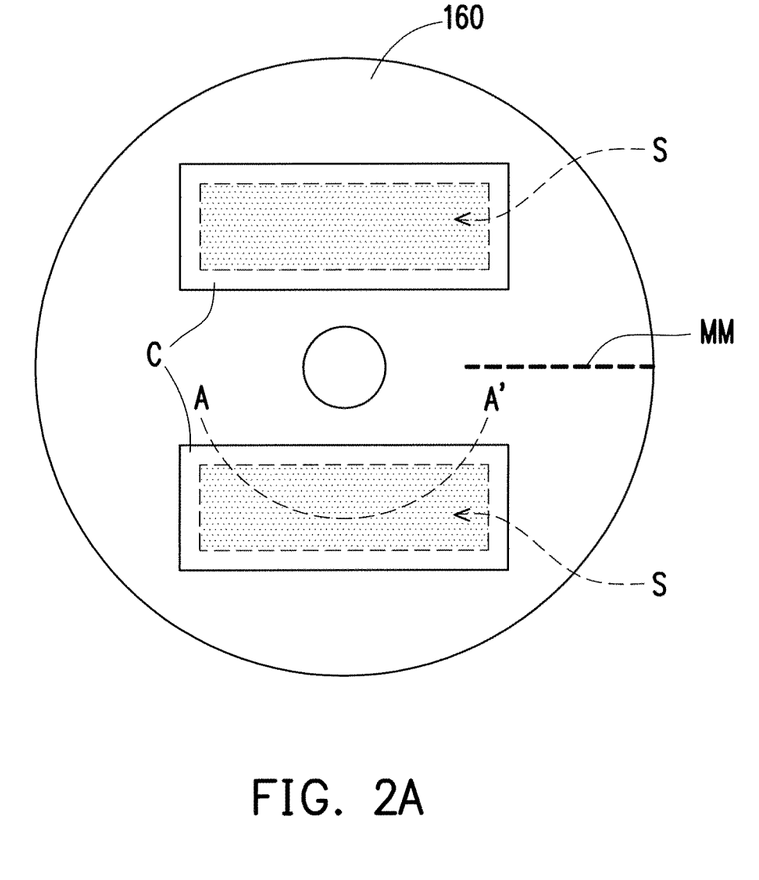
FIG. 2A is a schematic diagram depicting a sample in the embodiment of FIG. 1 of the present disclosure is located on a glass holder.
Figure 2B:
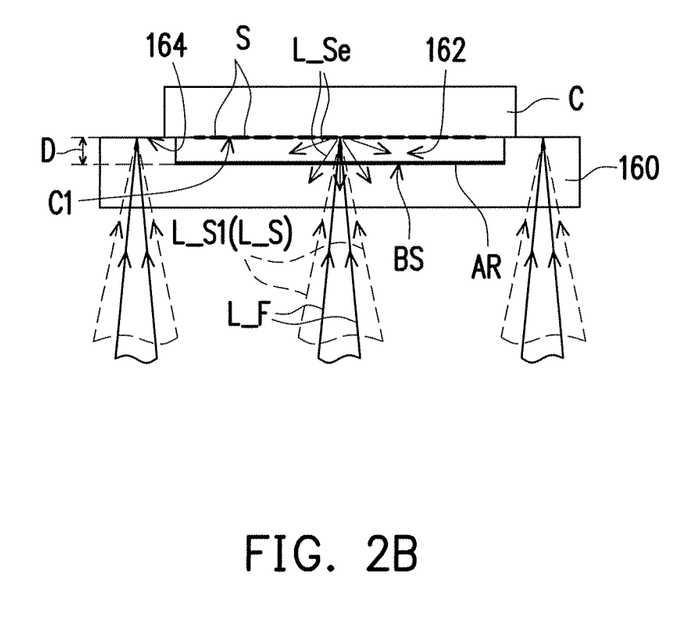
FIG. 2B is a side-view of the focusing light and the scanning light scanning along the trace of A-A' in FIG. 2A.

FIG. 2A is a schematic diagram depicting a sample in the embodiment of FIG. 1 of the present disclosure is located on a glass holder, and FIG. 2B is a side-view of the focusing light L_F and the scanning light L_S scanning along the trace of A-A' in FIG. 2A. In the embodiment, the optical scanning system 100 further includes a glass holder 160, disposed above or below the at least one optical scanning head 110. The glass holder 160 has a cavity portion 162, and the glass holder 160 is configured to carry the chip C (and the sample S). To be specific, a position of the sample S on the chip C is corresponding to a position of the cavity portion 162, and the surface C1 of the chip C is facing the cavity portion 162. In the embodiment, the first optical guiding structure 114 is configured to guide the focusing light L_F to focus on a top surface 164 of the glass holder 160 and pass through the cavity portion 162, and guide the focusing light to focus on the surface C1 of the chip C. Besides, the first optical guiding structure 114 is configured to guide the at least one scanning light L_S to focus and pass from the top surface 164 of the glass holder 160 to the surface C1 of the chip C on the top of the cavity portion 162, and then focus back to top surface 164 of the glass holder 160 outside of the cavity. Besides, the secondary light L_Se emitted from sample S passes through the glass holder 160 and is received by the light receiving device 130.

Referring to FIG. 2B, in particular, the chip C is, for example, configured to carry the sample S and dispose the sample S on the glass holder 160. When the sample S is disposed on the top of the cavity portion 162 of the glass holder 160, the sample S is disposed between the chip C and the cavity portion 162. In the embodiment, the cavity portion 162 has a bottom surface BS opposite to the surface C1 of the chip C. The surface C1 and the bottom surface BS have a gap therebetween to avoid the sample S from contacting to the bottom surface BS, so that the sample S will not be damaged. A depth D of the cavity portion 162, i.e. a distance between the bottom surface BS and the surface C1 of the chip C is in a range of 3 micrometers to 15 micrometers, preferably, the depth D is in a range of 7 micrometers to 10 micrometers for example. However, in some embodiments, the depth D can be other value, which is not limited by the invention. In addition, the bottom surface BS has an anti-reflection layer AR to avoid the focusing light L_F, the scanning light L_S, and the secondary light L_Se from reflecting at the bottom surfaces BS when the focusing light L_F, the scanning light L_S, and the secondary light L_Se passing through the cavity portion 162.

In the embodiment, the glass holder 160 is a circular cartridge, and the circular cartridge is adapted to rotate, so that the chip C and the sample S move along a path perpendicular to the transmission path of the focusing light L_F and the at least one scanning light L_S, so that the sample S can be scanned by the focusing light L_F and the at least one scanning light L_S. To be specific, the optical scanning system 100 further includes a spindle motor Mo (shown in FIG. 1), configured to drive the glass holder 160 rotating along a rotating axis Ax (shown in FIG. 1). A mark MM is located on the top surface 164 of the glass holder 160 (the circular cartridge). When the glass holder 160 rotates so that the focusing light L_F travels to the mark MM, the mark MM reflects the focusing light L_F, and the control unit 116 (focusing photodetector of the control unit 116) receives the focusing light L_F reflected by the mark MM. Then, a light reflecting signal is generated. The position corresponding to the light reflecting signal can be a start position in each scanning circle when the scanning light L_S scanning on the glass holder 160 (the circular cartridge), and the light reflecting signal can be used as a start mark of a circular scan of the circular cartridge. In the embodiment, a width of the mark MM is, for example, 10 micrometers, and a length of the mark MM can cover the scanning region of the sample S. Besides, the mark MM is made of metal, semiconductor, or insulator with high reflectance to the focusing light L_F, the invention is not limited thereto. In some embodiment, a plurality of marks are located on the top surface 164 of the glass holder 160 (the circular cartridge), when the glass holder 160 rotates so that the focusing light L_F travels to the marks, the marks reflect the focusing light L_F, and the control unit 116 receives the focusing light L_F reflected by the marks. In addition, a plurality of light reflecting signals are generated to be used as a plurality of start marks of the different areas surrounded by the marks of a circular scan of the circular cartridge. In these embodiments, for example, the marks are made of metals, semiconductors, or insulators with high reflectance to the focusing light L_F, the invention is not limited thereto.

In particular, the signals obtained by scanning of the glass holder 160 in each circle are divided evenly in 360 degrees, so that the angle value of each signal point can be obtained. The movement of optical scanning head 110 is driven by stepper motor, and the optical scanning head 110 moves outward along the radial direction of the glass holder 160, so that the focal point of the focusing light L_F and the scanning light L_S also moves outward along the radial direction of the glass holder 160. When every time the focal point moves a specific distance, the measurement of a plurality of signal points in one circle can be completed. As a result, the measurement result of the signal points located on each position along the radial direction and located at each angle can be obtained. The coordinate positions of the signal points can be transformed to the coordinate positions in (x, y) coordinate system through coordinate transformation, so that the measurement result of the signal points can be utilized or transformed to the image of the sample S.

Figure 3:
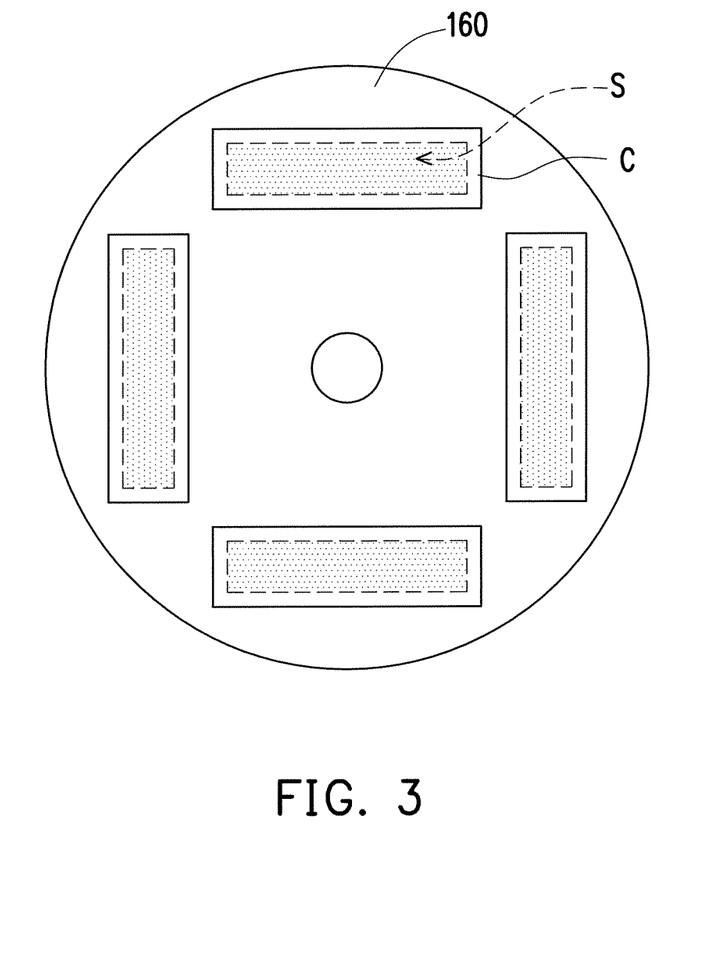
FIG. 3 to FIG. 4 are schematic diagrams depicting the sample is located on the glass holder in some embodiments of the present disclosure.
Figure 4:
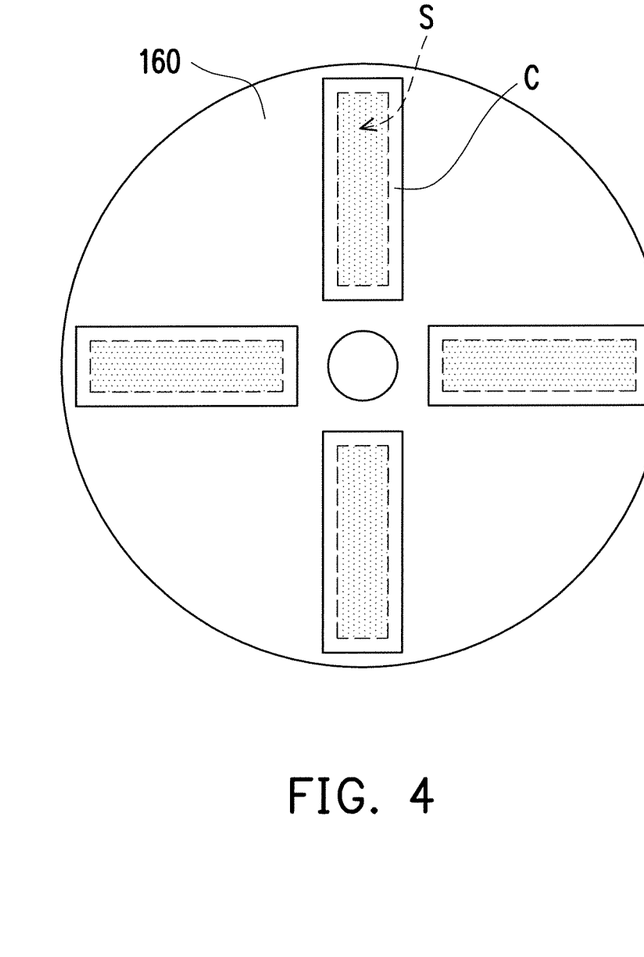
Figure 5A:
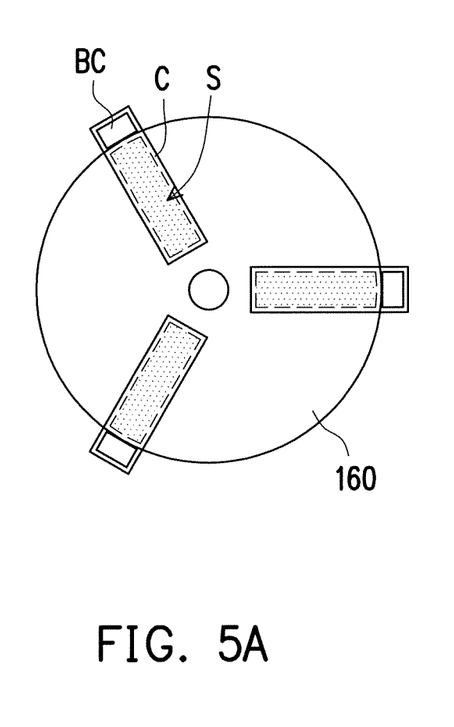
FIG. 5A to FIG. 5C are schematic diagrams showing the glass holder capable of putting 3, 4, and 6 chips with barcode labels located on the glass holder in some embodiments of the present disclosure.
Figure 5B:
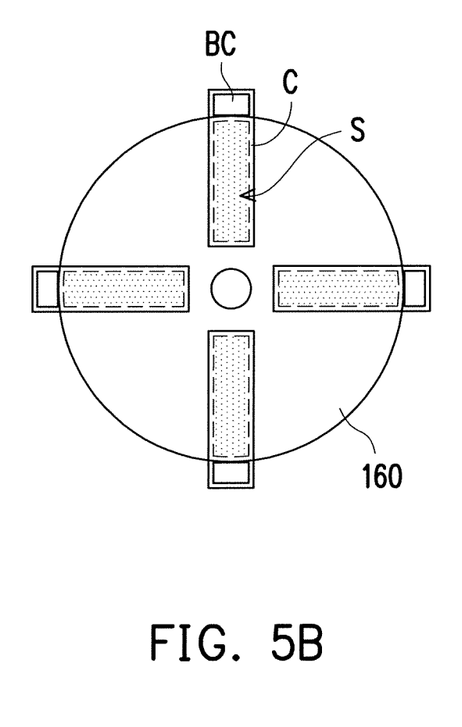
Figure 5C:
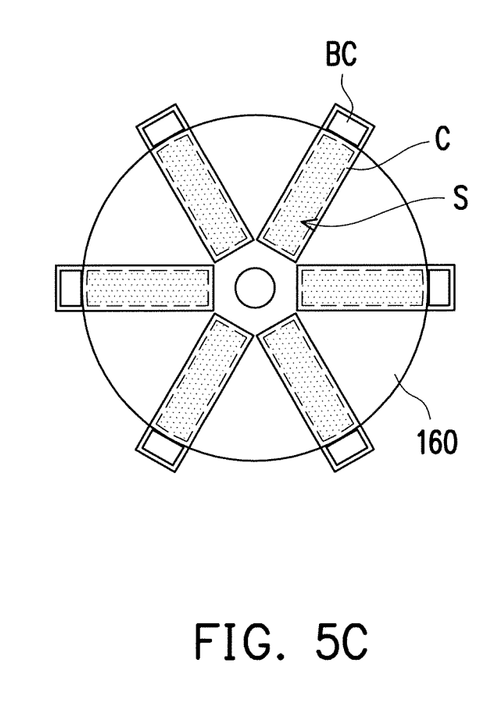

FIG. 3 to FIG. 4 are schematic diagrams depicting the sample is located on the glass holder 160 in some embodiments of the present disclosure. Referring to FIG. 3 and FIG. 4, to be specific, one or more chips C with sample S can be disposed on the glass holder 160 according to the requirement of actual optical scanning and detecting. The quantity of the chips C and the position that the chips C disposed on are not limited by the invention. FIG. 5A to FIG. 5C are schematic diagrams showing the glass holder capable of putting 3, 4, and 6 chips with barcode labels located on the glass holder in some embodiments of the present disclosure. Referring to FIG. 5A to FIG. 5C, to be specific, a barcode label BC is located on the surface of the chip (for example, the surface C1 of the chip C). When the circular cartridge (glass holder 160) rotates so that the focusing light L_F and the at least one scanning light L_S travel to a barcode of the barcode label BC, the secondary light L_Se is generated by the at least one scanning light L_S scanning over the barcode and is received by the light receiving device 130 for the barcode identification. In other words, the barcodes of the barcode labels BC can be read directly by using the scanning light sources 120. Besides, in some related embodiments, the chips C can be easily loaded into a slot of a metal cover plate and tightly pressed on the glass holder 160 through tightly pressing the chips C by the metal cover plate. The tension spring or sliding latch can be disposed to provide a pressure to the chips C, so that the chips C can be tightly pressed on the glass holder 160, which is not limited by the invention.

Figure 6:
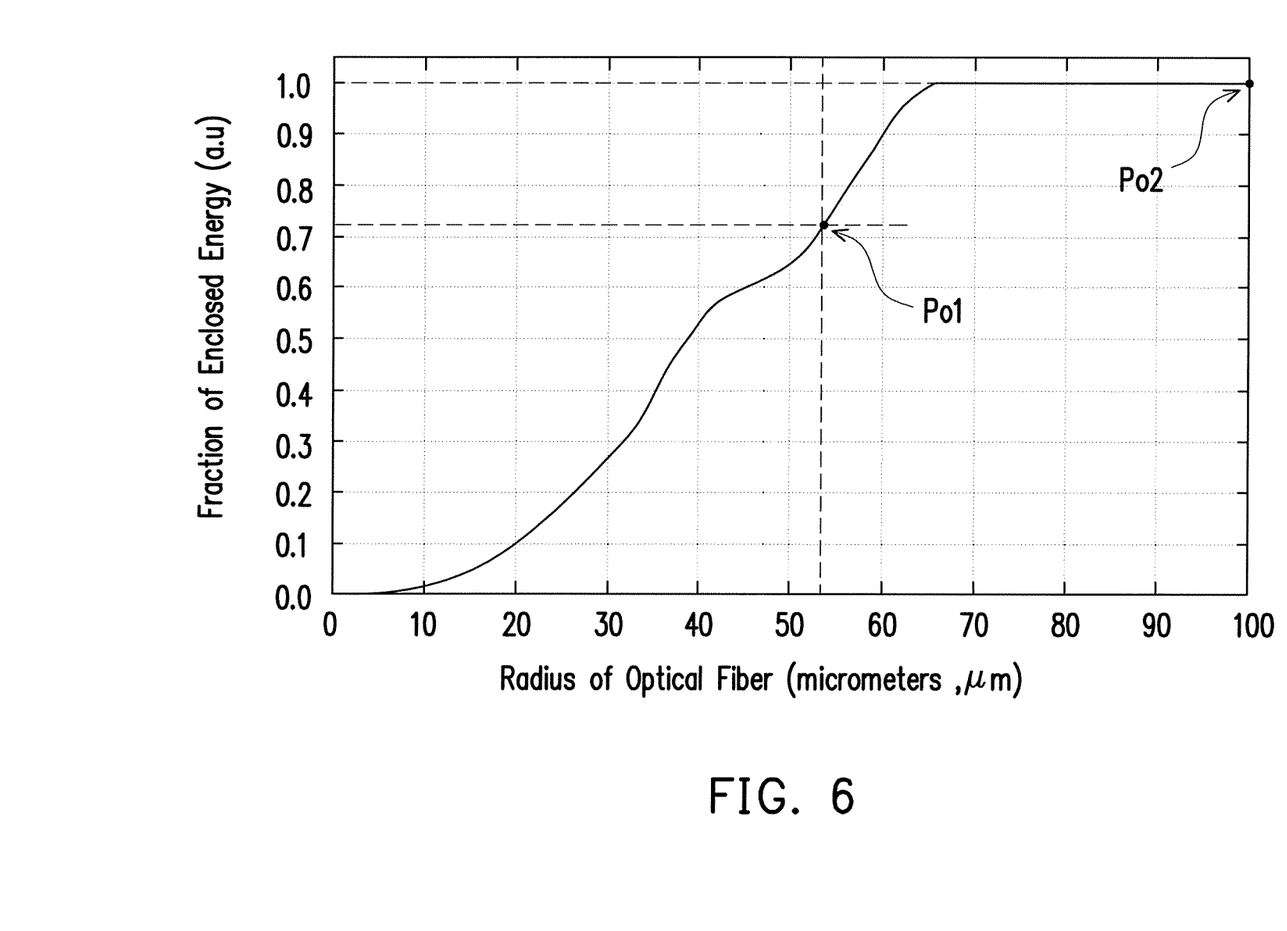
FIG. 6 is a schematic diagram of a fraction of enclosed energy of the secondary light entered in the optical fiber against the radius of the optical fiber.

FIG. 6 is a schematic diagram of a fraction of enclosed energy of the secondary light entered in the optical fiber OF against the radius of the optical fiber OF. Referring to FIG. 6, "Fraction of Enclosed Energy" of the longitudinal axis shows a ratio between the power of the secondary light L_Se after entering the optical fiber OF and the power of the secondary light L_Se before entering the optical fiber OF. "Radius of Optical Fiber" of the transverse axis shows a radius of the optical fiber OF, and the unit is micrometer. In FIG. 6, a first point Po1 shows that when the optical fiber OF with 105 micrometers in diameter (52.5 micrometers in radius) receives the secondary light L_Se, the light receiving efficiency is about 72%. Besides, a second point Pot shows that when the optical fiber OF with 200 micrometers in diameter (100 micrometers in radius) receives the secondary light L_Se, the light receiving efficiency is about 100%. To be specific, when the diameter of the optical fiber OF is designed larger, the light receiving efficiency of the secondary light L_Se is higher, however, the received noise is more, so that the signal-to-noise ratio (SNR) is affected. Although the smaller the diameter of the optical fiber OF is designed, the less noise it can be, the light receiving efficiency of the secondary light L_Se will be lower, and the alignment of the optical fiber OF will be difficult. In related embodiments, the diameter of the optical fiber OF is, preferably, in a range of 10 micrometers to 200 micrometers.

Figure 7A:
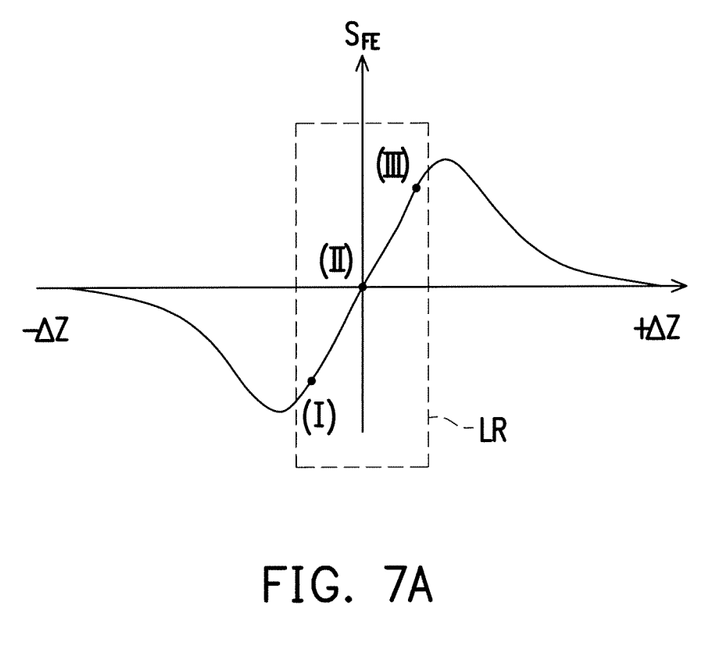
FIG. 7A to FIG. 7D shows a schematic diagram depicting the value of the focus error signal in different defocusing distances and a signal distribution of the focusing light on different regions of the photodetector.

FIG. 7A to FIG. 7D shows a schematic diagram depicting the value of the focus error signal $S_{FE}$ in different defocusing distances $\Delta Z$ and a signal distribution of the focusing light on different regions of the focusing photodetector of the control unit 116. In particular, the focusing photodetector of the control unit 116 includes four divided photoelectric detection areas, i.e., the photoelectric detection areas 602, 604, 606, 608. The signal value of the photoelectric detection area 602, the signal value of the photoelectric detection area 604, the signal value of the photoelectric detection area 606 and the signal value of the photoelectric detection area 608 are defined as A, B, C and D respectively. In addition, the value of the error signal $S_{FE}$ is defined in a linear region LR of S curve of FIG. 7A, and the value of the error signal $S_{FE}$ satisfies:

$$S_{FE}=(A+C)-(B+D) \qquad (1)$$

Figure 7B:
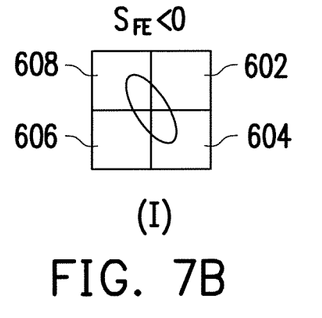
Figure 7C:
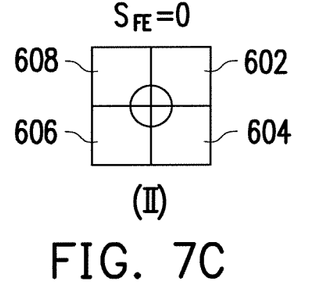
Figure 7D:
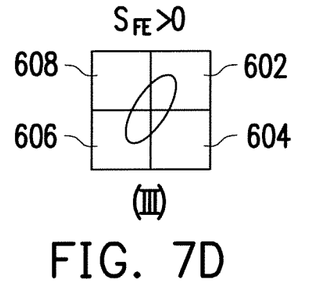

To be specific, when the focusing light L_F correctly focuses on the target, $S_{FE}$ is 0, as shown in FIG. 7C. When the focal point of the focusing light L_F is in front of the target, $S_{FE}$ is less than 0, as shown in FIG. 7B, and when the focal point of the focusing light L_F is behind the target, $S_{FE}$ is greater than 0, as shown in FIG. 7D. In related embodiments, when the photoelectric detection areas 602, 604, 606, 608 detect the focusing light L_F is out of focus, the focusing photodetector of the control unit 116 will, for example, send a servo signal to adjust the distance between the objective lens OL and the surface C1 of the chip C through the voice coil motor VCM disposed around the objective lens OL, so that the focusing light L_F will correctly focus on the target.

Figure 8A:
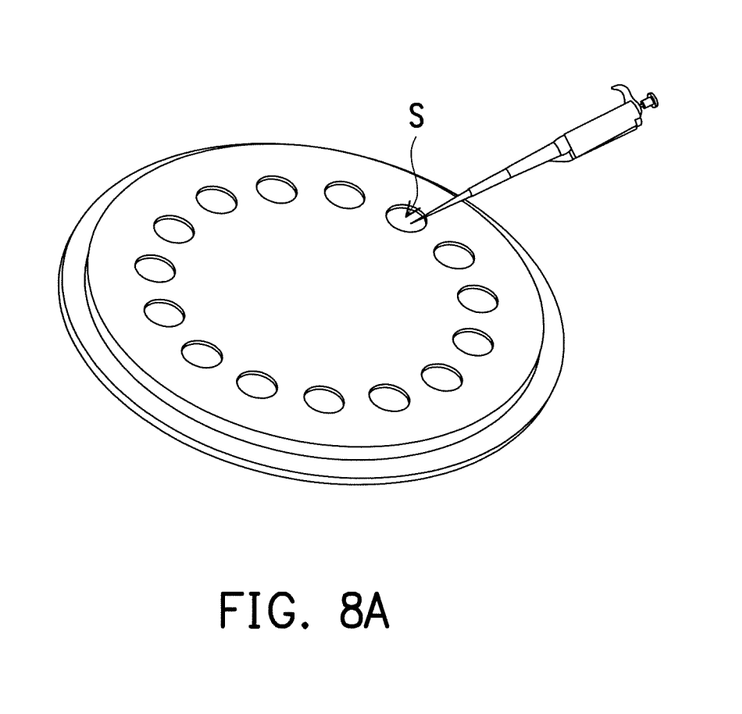
FIG. 8A to FIG. 8D are schematic diagrams depicting the optical scanning system scans the sample in some embodiments of the present disclosure.
Figure 8B:
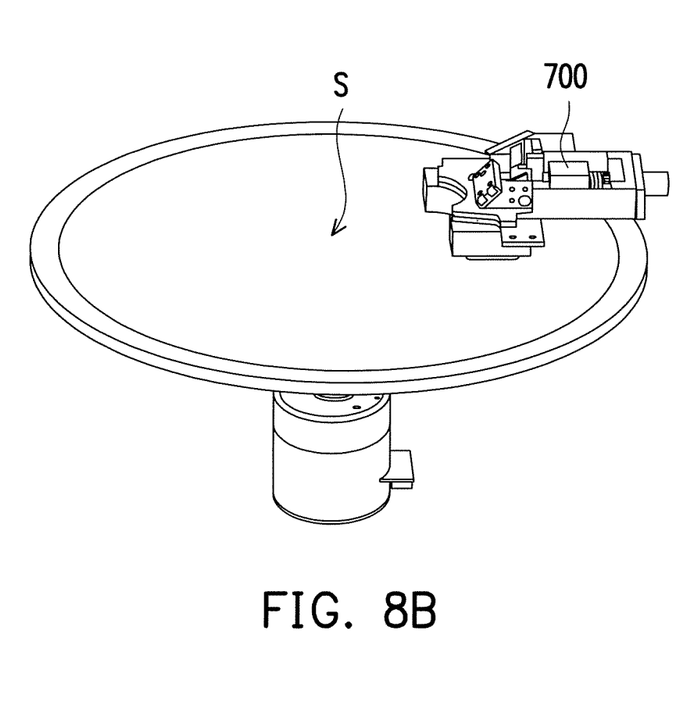
Figure 8C:
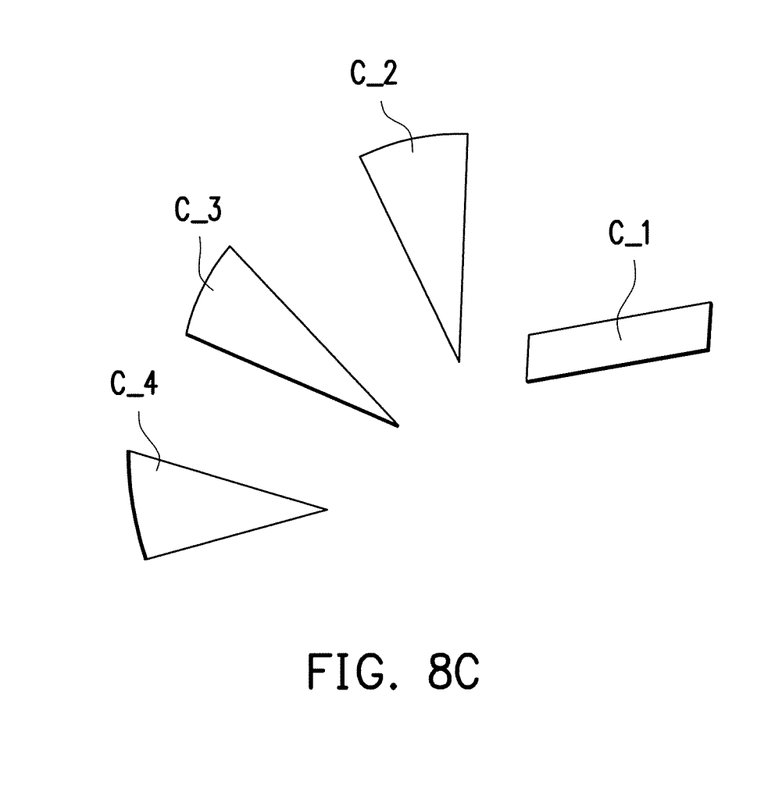
Figure 8D:
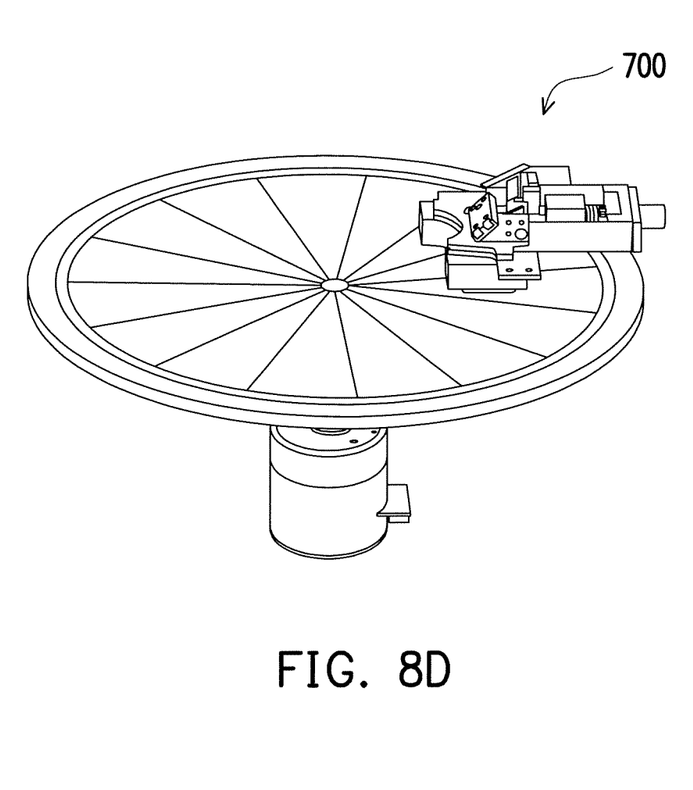

FIG. 8A to FIG. 8D are schematic diagrams depicting the optical scanning system scans the sample in some embodiments of the present disclosure. Referring to FIG. 8A to FIG. 8D, in these embodiments, the optical scanning system 700 is similar to the optical scanning system 100 in the embodiment of FIG. 1. Referring to FIG. 8B, the chip C is a disc-type chip, for example, a disc-type bio-microarray chip, and the optical scanning system 700 is further designed to be capable of directly scanning the sample S on the disc-type bio-microarray chip. The optical scanning system 700 is capable of performing large-area and fast scanning for the disc-type bio-microarray chip implanted directly on 2 inches to 12 inches glass, plastic or silicon wafers, and providing the scanning signal corresponding to the fluorescence for interpretation and analysis of backend data. In these embodiments, the disc-type bio-microarray chip includes a single reaction zone, or a plurality of reaction zones. For example, the disc-type bio-microarray chip can be divided in various reaction zones by a biocompatible organic partition board, like polylactic acid or polyglycolic acid and their derives, as shown in FIG. 8A, which is not limited by the invention. In addition, the disc-type bio-microarray chip can be divided into a plurality of small biochips with different shapes, as shown in FIG. 8C. After the small biochips carry out a biological reaction to form needed chips C_1, C_2, C_3, C_4, the chips C_1, C_2, C_3, C_4, can be re-assembled into a disc-like in order to facilitate a one-time scan of the optical scanning system 700, as shown in FIG. 8D, or the chips C_1, C_2, C_3, C_4 can be loaded in a cartridge for the separate detection, the invention is not limited thereto.

Figure 9:
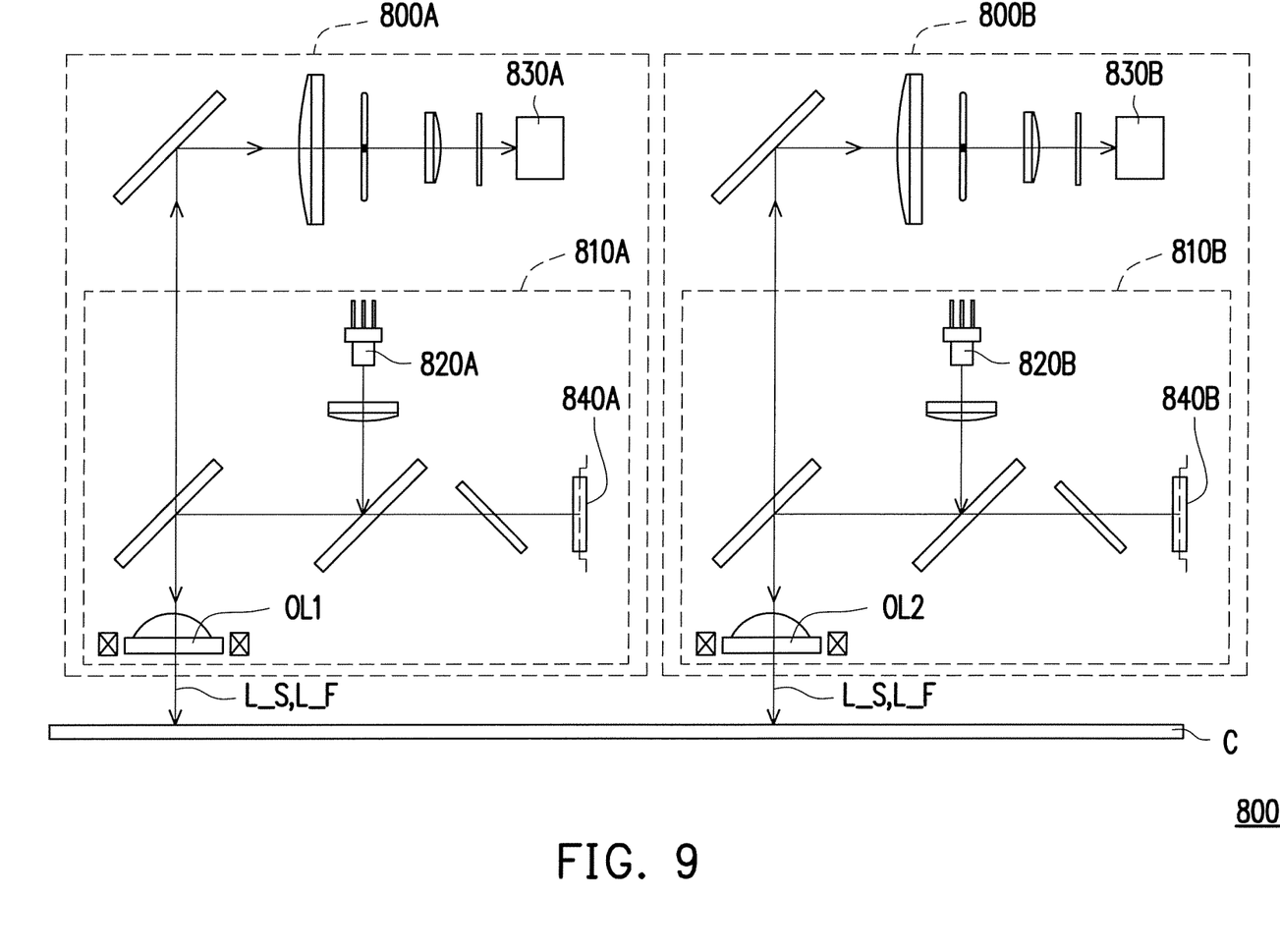
FIG. 9 is a schematic diagram of an optical scanning system in another embodiment of the present disclosure.

FIG. 9 is a schematic diagram of an optical scanning system in another embodiment of the present disclosure. Referring to FIG. 9, in the embodiment, the optical scanning system 800 is similar to the optical scanning system in the embodiment of FIG. 1. The differences between the optical scanning system 800 and the optical scanning system 100 are as follows. The optical scanning system 800 is, for example, designed to be capable of directly scanning the sample (not shown) located on the disc-type chip C, like the optical scanning system 700. The optical scanning system 800 includes an optical scanning unit 800A and an optical scanning unit 800B, and the at least one optical scanning head of the optical scanning system 800 includes a first optical scanning head 810A in the optical scanning unit 800A and a second optical scanning head 810B in the optical scanning unit 800B. Besides, the position on the surface of the chip C the focusing light L_F of the first optical scanning head 810A focuses on is different from the position on the surface S1 of the chip C the focusing light L_F of the second optical scanning head 810B focuses on.

To be specific, each of the optical scanning unit 800A and the optical scanning unit 800B includes an optical scanning head, and the optical scanning system 800 has two optical scanning heads. Besides, each of the optical scanning unit 800A and the optical scanning unit 800B has the focusing light source and the scanning light source. In the present embodiment, the focusing light source and the scanning light source are the same one for the optical scanning unit 800A and the optical scanning unit 800B. To be specific, the optical scanning unit 800A includes, for example, the light source 820A with the scanning and focusing functions, the objective lens OL1, the light receiving device 830A, the control unit 840A including the focusing photodetector, and other optical members, and the optical scanning unit 800B includes, for example, the light source 820B with the scanning and focusing functions, the objective lens OL2, the light receiving device 830B, the control unit 840B including the focusing photodetector, and other optical members. In the embodiment, the scanning light L_S emitted by the scanning light source 820A is, for example, a laser light having a 635 nanometers wavelength, and the scanning light L_S emitted by the scanning light source 820B is, for example, a laser light having a 520 nanometers wavelength. To be specific, in the embodiment, the secondary light (fluorescence) excited by the scanning light L_S emitted by the scanning light source 820A will not interfere the secondary light excited by the scanning light L_S emitted by the scanning light source 820B. Besides, the optical scanning system 800 can perform multi-light-source scanning on different positions of the surface of the sample located on the chip C or of the surface of the circular cartridge in the same time, so that the overall scan time will be saved. In related embodiments, the optical scanning system may include one or more optical scanning heads, and each optical scanning head may include one or more scanning and focusing light sources, to achieve the combination of the scanning lights having different wavelengths, which is not limited by the invention.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. An optical scanning system adapted to scan a sample on a chip, the optical scanning system comprising:
   at least one optical scanning head, wherein each of the at least one optical scanning head comprises a focusing light source, a first optical guiding structure and a control unit coupled to the first optical guiding structure, wherein the focusing light source is adapted to emit a focusing light, the first optical guiding structure is disposed on a transmission path of the focusing light, and configured to guide the focusing light to travel to the sample;
   at least one scanning light source, adapted to emit at least one scanning light, wherein the first optical guiding structure is configured to guide the at least one scanning light to the sample to generate a secondary light, wherein the control unit is configured to control the first optical guiding structure to keep the focusing light and the at least one scanning light focusing on a surface of the chip;
   a light receiving device, disposed on a transmission path of the secondary light to receive the secondary light and generate a scanning electronic signal, wherein the light receiving device comprises a photon multiplex tube;

a processor, electrically coupled to the light receiving device to dispose the scanning electronic signal; and a glass holder, disposed on the transmission path of the focusing light and above or under the at least one optical scanning head, wherein the glass holder has a cavity portion, and the glass holder is configured to carry the chip, wherein a depth of the cavity portion is in a range of 3 micrometers to 15 micrometers, wherein a position of the sample on the chip is corresponding to a position of the cavity portion, and the surface of the chip is facing the cavity portion, wherein the first optical guiding structure comprises an objective lens, the focusing light and the at least one scanning light pass through the objective lens, and the focusing light and the at least one scanning light focus on an identical focal point, wherein the control unit is configured to adjust a distance between the objective lens and the sample so as to keep the focal point located on the surface of the chip, wherein the first optical guiding structure is configured to guide the focusing light to focus on a top surface of the glass holder and pass through the cavity portion, and guide the focusing light to focus from the glass holder to the surface of the chip, and the first optical guiding structure is configured to guide the at least one scanning light to scan from the top surface of the glass holder to the surface of the chip, wherein the secondary light passes through the cavity portion and the glass holder along the transmission path of the secondary light, and is received by the light receiving device.

2. The optical scanning system as claimed in claim 1, further comprising a second optical guiding structure, disposed on the transmission path of the secondary light, wherein the second optical guiding structure comprises a focusing lens, wherein the focal point the focusing light and the at least one scanning light focus on is a first focal point, and the second optical guiding structure focuses the secondary light on a second focal point, wherein the first focal point and the second focal point form conjugate focal points.

3. The optical scanning system as claimed in claim 2, wherein the second optical guiding structure further comprises an optical fiber, the focusing lens is configured to focus the secondary light on the second focal point, an end of the optical fiber is located on the second focal point to receive the secondary light.

4. The optical scanning system as claimed in claim 3, wherein a diameter of the optical fiber is in a range of 10 micrometers to 200 micrometers.

5. The optical scanning system as claimed in claim 2, wherein the second optical guiding structure further comprises a pinhole device, the focusing lens is configured to focus the secondary light on the second focal point, the pinhole device has a pinhole, and the second focal point is located at the pinhole, wherein the pinhole device allows the secondary light passed through the second focal point passing through the pinhole.

6. The optical scanning system as claimed in claim 1, wherein a bottom surface of the cavity portion has an anti-reflection layer.

7. The optical scanning system as claimed in claim 1, wherein the glass holder is a circular cartridge, and the circular cartridge is adapted to rotate so that the sample is scanned by the focusing light and the at least one scanning light.

8. The optical scanning system as claimed in claim 7, wherein at least one mark is located on a top surface of the circular cartridge, when the circular cartridge rotates so that the focusing light travels to the at least one mark, the at least one mark reflects the focusing light, and the control unit receives the focusing light reflected by the at least one mark, wherein at least one light reflecting signal is generated to be used as at least one start mark of a circular scan of the circular cartridge.

9. The optical scanning system as claimed in claim 8, wherein the at least one mark is made of metal, semiconductor, or insulator with high reflectance to the focusing light.

10. The optical scanning system as claimed in claim 7, wherein a barcode label is located on the surface of the chip, when the circular cartridge rotates so that the focusing light and the at least one scanning light travel to a barcode of the barcode label, the secondary light is generated by the at least one scanning light scanning over the barcode and is received by the light receiving device for the barcode identification.

11. The optical scanning system as claimed in claim 1, wherein the at least one scanning light source comprising a first scanning light source and a second scanning light source, the first scanning light source is adapted to emit a first scanning light, and the second scanning light source is adapted to emit a second scanning light, wherein the first optical guiding structure is configured to guide the first scanning light to the sample to generate a first secondary light, and the first optical guiding structure is configured to guide the second scanning light to the sample to generate a second secondary light, wherein a wavelength of the first scanning light is different from a wavelength of the second scanning light.

12. The optical scanning system as claimed in claim 1, wherein the at least one optical scanning head comprising a first optical scanning head and a second optical scanning head, a position on the surface of the chip that the focusing light of the first optical scanning head focuses on is different from a position on the surface of the chip that the focusing light of the second optical scanning head focuses on.

13. The optical scanning system as claimed in claim 1, wherein the chip is a disc-type chip, and the optical scanning system s capable of directly scanning the sample located on the disc-type chip, the disc-type chip includes a single reaction zone, or a plurality of reaction zones divided by a biocompatible organic partition board.

14. The optical scanning system as claimed in claim 13, wherein the disc-type chip is a disc-type bio-microarray chip, and the disc-type bio-microarray chip is divided into a plurality of small biochips with different shapes, wherein after the small biochips carry out a biological reaction, the small chips are re-assembled into a disc-like in order to facilitate a one-time scan of the optical scanning system, or the small chips are loaded in a cartridge for a separate detection.

15. The optical scanning system as claimed in claim 1, wherein the chip is a biochip, and the sample is a biological sample.

* * * * *